United States Patent [19]

Umezawa et al.

[11] 4,358,602

[45] Nov. 9, 1982

[54] EBELACTONES AND PRODUCTION THEREOF

[75] Inventors: Hamao Umezawa, Tokyo; Takaaki Aoyagi, Fujisawa; Tomio Takeuchi, Tokyo; Masa Hamada, Tokyo; Shinichi Kondo, Yokohama; Masaaki Ishizuka, Tokyo, all of Japan

[73] Assignee: Zaidan Hojin Biseibutsu Kagaku Kenkyu Kao, Tokyo, Japan

[21] Appl. No.: 240,457

[22] Filed: Mar. 4, 1981

[30] Foreign Application Priority Data

Mar. 14, 1980 [JP] Japan ............................ 55-31514

[51] Int. Cl.³ .................... C07D 305/12; C12P 17/02
[52] U.S. Cl. .................................. 549/328; 435/123

[58] Field of Search ................. 435/123; 260/343.9; 549/328

[56] References Cited

U.S. PATENT DOCUMENTS 4,242,453 12/1980 Umezawa et al. ................. 435/123

Primary Examiner—John M. Ford
Attorney, Agent, or Firm—Larson and Taylor

[57] ABSTRACT

New physiologically active substances, ebelactone A and ebelactone B which are generally termed ebelactone are produced from a new microorganism, Streptomyces MG7-G1 strain identified FERM-P 5363 or ATCC No. 31860 and ATCC No. 31880. Ebelactone is useful as a host defense stimulator having an activity to enhance cell-mediated immunity, and also as an anti-inflammatory agent.

9 Claims, No Drawings

EBELACTONES AND PRODUCTION THEREOF

SUMMARY OF THE INVENTION

This invention relates to new physiologically active compounds, named ebelactone A and ebelactone B, having immunopotentiating properties and anti-inflammatory properties, to the process for the production thereof and to uses thereof as the host defense stimulator and as the anti-inflammatory agent in living animals and humans.

BACKGROUND OF THE INVENTION

Many strains of the genus Streptomyces produce therapeutically useful substances, such as antibiotics. Some substances useful as the host defense stimulator or immunopotentiator or as the anti-inflammatory agent are known, but there remains a need for a more effective agents useful for therapeutic treatment of various diseases in living animals, including humans.

An object of this invention is to provide new compounds which are useful as the immunopotentiator and/or the anti-inflammatory agent. A further object of this invention is to provide a process for the fermentative production of these new compounds. Other objects will be clear from the following descriptions.

We have made extensively our research in an attempt to produce and obtain new physiologically active compounds. As a result, we have now found that when a new strain of the genus Streptomyces which was isolated from a soil sample collected from the ground of Rissho University in Kumagaya City, Saitama Prefecture, Japan and which was alloted a laboratory designation, Streptomyces MG7-G1 strain, is cultivated in a culture medium under aerobic conditions, there are produced and accumulated in the culture new substances which show the activities inhibitory to esterase and formylmethionine aminopeptidase. We have succeeded to isolate these new substances from the culture and purify them. From the chemical, physical and biological studies of these isolated substances, it has been confirmed that each of these isolated substances is a new compound which is low toxic and which is distinguishable from any of the known compounds. Thus, we have denominated these two new compounds as ebelactone A and ebelactone B, respectively. Ebelactones A and B have the new chemical structures and physico-chemical properties as described later.

DETAILED DESCRIPTION OF THE INVENTION

According to a first aspect of this invention, there is provided as the new compound, ebelactone which is selected from ebelactone A and ebelactone B and which is represented by the general formula

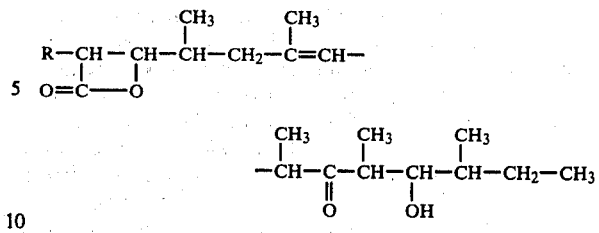

wherein R is methyl group —CH₃ for ebelactone A and ethyl group —CH₂CH₃ for ebelactone B.

Herein, by the term ebelactone is meant ebelactone A or ebelactone B or a mixture of them, unless otherwise stated. This invention embraces ebelactone A and ebelactone B, either alone or in a mixture of them, which may be present in a dilute solution, as a crude concentrate, as a crude solid or as a purified solid.

We have further made our research on utilities of ebelactone as a medicine, and we have now found that ebelactone exhibits not only an activity to enhance the cell-mediated immune response in living animals but also an activity to inhibit the inflammations in living animals. In these circumstances, ebelactone is promising to be useful in many and various therapeutic applications, by utilizing the biological properties of ebelactone, for example, in the field of immunological treatment of tumors and as an agent for enhancing the anti-tumor agents such as bleomycins.

We have tested whether ebelactone is inhibitory to the enzymatic activity of an esterase to degrade p-nitrophenyl acetate and the enzymatic activity of a formylmethionine aminopeptidase to degrade N-formylmethionine β-naphthylamide, and it has been revealed that ebelactone has the anti-esterase activity and the anti-formylmethionine aminopeptidase activity in combination, as demonstrated by the experiments given hereinafter. Thus, ebelactone A and ebelactone B both have the anti-esterase activity and the anti-formylmethionine aminopeptidase activity and are represented by the following chemical structures, respectively.

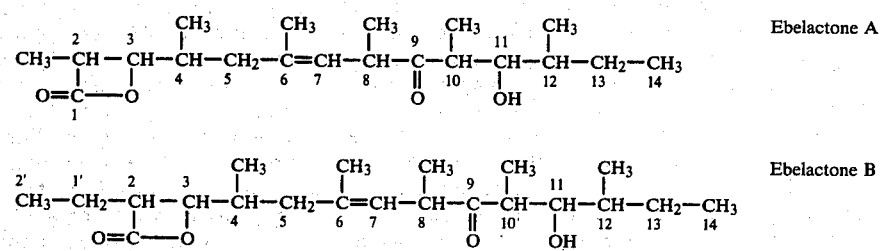

Ebelactones A and B both are obtained in the form of colorless crystals generally by cultivating an ebelactone-producing strain in a culture medium, extracting the resulting culture broth filtrate with a water-immiscible organic solvent, fractionating the organic extract chromatographically on silica gel or in any suitable way and then concentrating the active fractions containing ebelactone, followed by chromatographic isolation of ebelactones A and B.

Physico-chemical properties of ebelactone are described below.

Ebelactone A is a neutral compound which is colorless and crystalline and shows a melting point of 86° C. and a specific optical rotation $[\alpha]_D^{20} - 221°$ (c=1, methanol). The molecular weight is 338 as determined by mass spectrometry, and the elemental analysis is C 70.97, H 10.20, O 19.07% and is coincident with the theoretical values of the molecular formula $C_{20}H_{34}O_4$. The ultra-violet spectrum of ebelactone A shows an absorption peak at $\lambda_{max}^{MeOH}$ 291 nm ($\epsilon$311). The infrared absorption spectrum of ebelactone A pelleted in potassium bromide shows the characteristic absorption peaks at 3500, 2950, 1825, 1695, 1460, 1385, 1125, 980 and 870 cm$^{-1}$. In the proton nuclear magnetic resonance absorption spectrum ($\delta$ppm) of ebelactone A in deutro-chloroform, there are shown peaks at 1.38 (2—CH$_3$), 3.29 (CH of C-2), 3.88 (CH of C-3), 0.87 (4—CH$_3$) ~1.99 (CH of C-4), ~1.7 and 2.35 (CH$_2$ of C-5), 1.73 (6—CH$_3$), 5.04 (CH of C-7), 1.12 (8—CH$_3$), 3.59 (CH of C-8), 1.10 (10—CH$_3$), 2.86 (CH of C-10), 3.50 (CH of C-11), 3.03 (11—OH), 0.79 (12—CH$_3$), ~1.41 (CH of C-12), ~1.71 (CH$_2$ of C-13) and 0.87 (CH$_3$ of C-14).

Ebelactone B is also a neutral compound which is colorless and crystalline and shows a melting point of 77° C. and a specific optical rotation $[\alpha]_D^{26}$ —203° (c=1, methanol). The molecular weight is 352 as determined by mass spectrometry, and the elemental analysis is C 71.72, H 10.31, O 18.37% and is coincident with the theoretical values of the molecular formula $C_{21}H_{36}O_4$. The ultraviolet absorption spectrum of ebelactone B shows an absorption peak at $\lambda_{max}^{MeOH}$ 291 nm ($\epsilon$479). The infrared absorption spectrum of ebelactone B pelleted in potassium bromide shows characteristic absorption peaks at 3500, 2960, 1825, 1700, 1465, 1390, 1125, 1000, 970 and 870 cm$^{-1}$. In the proton nuclear magnetic resonance absorption spectrum ($\delta$ppm) of ebelactone B in deutero-chloroform, there are shown peaks at 1.06 (CH$_3$ of C-2'), ~1.86 (CH$_2$ of C-1'), 3.20 (CH of C-2), 3.92 (CH of C-3), 0.86 (4—CH$_3$), ~2 (CH of C-4), ~1.86 and 2.38 (CH$_2$ of C-5), 1.73 (6—CH$_3$), 5.04 (CH of C-7), 1.12 (8—CH$_3$), 3.58 (CH of C-8), 1.10 (10—CH$_3$), 2.86 (CH of C-10), 3.51 (CH of C-11), 3.04 (11—OH), 0.78 (12—CH$_3$), ~1.43 (CH of C-12), ~1.73 (CH$_2$ of C-13) and 0.87 (CH$_3$ of C-14).

According to a second aspect of this invention, there is provided a process for the production of an ebelactone, which comprises cultivating an ebelactone-producing strain of the genus Streptomyces under aerobic conditions in a culture medium containing assimilable carbon and nitrogen sources for a sufficient time to produce and accumulate ebelactone in the culture medium. This process may include further the step of recovering the ebelactone from the culture obtained.

According to an embodiment of this second aspect invention, there is provided a process of producing ebelactone A which comprises cultivating an ebelactone A-producing strain of the genus Streptomyces under aerobic conditions in a culture medium containing assimilable carbon and nitrogen sources for a sufficient time to produce and accumulate ebelactone A in the culture. According to an another embodiment, there is provided a process of producing ebelactone B, which comprises cultivating an ebelactone B-producing strain of the genus Streptomyces under aerobic conditions in a culture medium containing assimilable carbon and nitrogen sources for a sufficient time to produce and accumulate ebelactone B in the culture. The process of the second aspect invention includes further the step of recovering from the culture ebelactone A and ebelactone B, either alone separately or in the form of a mixture or as a crude product or a purified product.

As an example of the ebelactone-producing strain, there is mentioned a strain of the genus Streptomyces which was isolated by the present inventors from a soil sample collected in the ground of Rissho University, at Kumagaya City, Saitama Prefecture, Japan and which is designated as Streptomyces MG7-G1 strain.

This MG7-G1 strain has the following microbiological properties.

1. Microscopical morphology

Microscopic observations show that the MG7-G1 strain produces branched substrate mycelium. Relatively long and rectiflexibilis aerial hyphae develops from the substrate mycelium. No spirals or whorl branching is observed. The matured aerial hyphae bears a chain of 10 or more spores. The dimensions of spore is 0.6~0.8 microns wide×0.8~1.2 microns long. Under electron microscope, the surface of spore is smooth.

2. Cultural characteristics on different culture media

The color standard given in brackets below is according to the color standard set forth in the "Color Harmony Manual" published by Container Corporation of America, unless otherwise stated.

(1) On sucrose-nitrate agar medium (incubated at 27° C.): Colorless to pale yellow (2 ec, biscuit) to pale yellowish brown (2 gc, bamboo) growth with aerial hyphae which is brownish white (3 ec, light beige) to brownish gray (3 ig, beige brown) in color. No diffusible pigment is observed.

(2) On glucose-asparagine agar medium (incubated at 27° C.): Colorless to pale yellow to pale yellowish brown (2 nl, covert brown) growth with aerial hyphae which is brownish white to bright brownish gray (3 ml, beaver gray) to bright gray (2 fe, covert gray) in color. About 14 days of the incubation, there is produced diffusible pigment which is faintly tinged with brown.

(3) On glycerine-asparagine agar medium (ISP-medium 5, incubated at 27° C.): Pale yellow to pale yellowish brown (2 ie, light mustard tan) to grayish yellow brown (2 li, covert brown) to dark brown (3 nl, dark brown) growth on which is formed aerial pyphae of grayish white (2 dc, natural) to bright gray (2 fe, covert gray) to brownish gray (3 ig, beige brown) in color. About 10 days of the incubation, there is produced diffusible pigment which is faintly tinged with brown.

(4) On starch-inorganic salt agar medium (ISP-medium 4, incubated at 27° C.): Pale yellow to pale yellowish brown (2 ie, light mustard tan) to yellow brown (3 li, beaver) growth on which is formed aerial hyphae of brownish white to bright gray (2 fe, covert gray) to brownish gray (3 ih, beige gray) in color. About 10 days of the incubation, there is produced diffusible pigment which is faintly tinged with brown.

(5) On tyrosine agar medium (ISP-medium 7, incubated at 27° C.): Pale yellowish brown to yellowish brown (2 ni, mustard brown) growth on which is formed aerial hyphae of yellowish gray to bright gray (2 fe, covert gray) in color. About 5 days of the incubation, there is produced diffusible pigment which is tinged with brown.

(6) On nutrient agar medium (incubated at 27° C.): Pale yellowish brown to bright brown (3 lg, light brown) growth without or with slight and brown-tinged formation of aerial hyphae. Brown colored diffusible pigment is produced.

(7) On yeast extract-malt extract agar medium (ISP-medium 2, incubated at 27° C.): Pale yellowish brown to gray-tinged yellowish brown (2 nl, covert brown)

growth on which is formed aerial hyphae of grayish white to bright gray (2 fe, covert gray) to brownish gray (2 ih, dark covert gray) in color. Brown colored diffusible pigment is produced.

(8) On oat-meal agar medium (ISP-medium 3, incubated at 27° C.): Pale yellowish brown (2 ie, light mustard tan) growth with aerial hyphae which is yellow-tinged gray to bright gray (2 fe, covert gray) to brownish gray (2 ih, dark covert gray) in color. About 21 days of the incubation, there is produced diffusible pigment which is faintly tinged with brown.

(9) On glycerine-nitrate agar medium (incubated at 27° C.): Pale yellow to pale yellowish brown to yellowish brown (3 li, beaver) growth with aerial hyphae which is grayish white to bright gray (2 li, covert brown) to gray (3 ih, beige gray) in color. About 6 days of the incubation, there is produced diffusible pigment which is faintly tinged with brown.

(10) On starch agar medium (incubated at 27° C.): Colorless to pale yellow to yellowish brown (2 lg, mustard tan) growth on which is formed aerial hyphae of grayish white to bright gray (3 fe, silver gray) to brownish gray (3 ih, beige gray) in color. About 10 days of the incubation, there is produced diffusible pigment which is faintly tinged with brown.

(11) On calcium malate agar medium (incubated at 27° C.): Pale yellow growth with aerial hyphae which is grayish white to brownish gray (3 ig, beige brown) in color. No diffusible pigment is observed.

(12) On cellulose medium (incubated at 27° C.): Colorless growth. Neither aerial hyphae nor diffusible pigment are observed.

(13) On gelatine stab medium: on plain gelatine medium (incubated at 20° C.), pale yellow to pale yellowish brown growth on which is slightly formed aerial hyphae of brownish white tinge, and brown diffusible pigment is produced. While, on glucose-peptone-gelatine medium (incubated at 27° C.), pale yellowish brown growth without aerial hyphae. There is produced diffusible pigment which is faintly tinged with brown.

(14) On skimmed milk medium (incubated at 37° C.): pale yellow to pale brown to yellowish brown growth without aerial hyphae. There is produced diffusible pigment which is slightly tinged with brown.

3. Physiological properties (1) Temperature for growth: grow at 20° C., 24° C., 27° C., 30° C. and 37° C. but not at 50° C. when tested at these temperatures on glucose-asparagine agar medium. It appears that the optimum temperature for good growth is in the range of 24° C. to 30° C.

(2) Liquefaction of gelatine

When incubated at 20° C. on 15% plain gelatine medium and when incubated at 27° C. on glucose-peptone-gelatine medium, the liquefaction starts about 6 days of the incubation in both cases to a medium degree.

(3) Hydrolysis of starch

When incubated at 27° C. on starch-inorganic salt agar medium and when incubated at 27° C. on starch agar medium, the hydrolysis of starch starts significantly about 6 days of the incubation to a medium or strong degree.

(4) Coagulation and peptonization of skimmed milk (incubated at 37° C.): Coagulation starts about 5 days of the incubation and is completed at the end of 7 days of the incubation, immediately followed by the peptonization. The peptonization is completed at the end of 14 days of the incubation. Degree of the peptonization is medium to strong.

(5) Formation of melanoid pigment (incubated at 27° C. on trypton-yeast-extract-broth, ISP-medium 1; incubated at 27° C. on peptone-yeast extract-iron agar, ISP-medium 6; and incubated at 27° C. on tyrosine agar, ISP-medium 7):

Formation of melanoid pigment is observed on trypton-yeast extract-broth medium and on tyrosine agar medium. This MG7-G1 strain does not grow on the peptone-yeast extract-iron agar medium, but this strain grows and produces melanoid pigment on such medium which is obtained by removing the iron ammonium citrate component out of the peptone-yeast extract-iron agar medium.

(6) Utilization of carbon sources for growth (estimated in Pridham-Gottlieb medium, ISP-medium 9, when incubated at 27° C.).

Glucose is utilized for growth. L-Arabinose, D-xylose, D-fructose, sucrose, inositol, L-rhamnose, raffinose and D-mannitol are not utilized.

(7) Dissolution of calcium malate (incubated at 27° C. on calcium malate agar medium).

About 6 days of the incubation, the calcium malate starts to be dissolved around the growth, and degree of the dissolution is medium to strong.

(8) Reduction of nitrate (estimated in aqueous peptone solution containing 1.0% potassium nitrate, ISP-medium 8, when incubated at 27° C.): Negative.

Summarizing the above-mentioned characteristics of the MG7-G1 strain, it is noted that this strain belongs to the genus Streptomyces and is characterized by the absence of whorls or spirals on the aerial hyphae and also by the smooth surface of the spore.

It is further noted that on various culture media, the MG7-G1 strain gives pale yellow to pale yellowish brown to yellowish brown colored growth with aerial hyphae of grayish white to bright gray to brownish gray in color and produces diffusible pigment which is faintly tinged with brown, and that this strain shows a positive chromogenicity, a medium degree of proteolysis and a medium to strong degree of hydrolysis of starch.

On the basis of the above-mentioned properties of the MG7-G1 strain, this strain is compared to known species of Streptomyces with reference to the description in the four literatures: H. Nishimura et al "Journal of Antibiotics" Ser. A, Vol. 10, page 205 (1957); Bergy's Manual of Determinative Bacteriology, 8th Edition, page 761; "International Journal of Systematic Bacteriology" Vol. 18, No. 4, page 284 (1968); and the Actinomycetes Vol. 2, page 166. Characteristics of the MG7-G1 strain resemble most closely those of *Streptomyces aburaviensis*.

A culture sample of *Streptomyces aburaviensis* was obtained and directly compared with the MG7-G1 strain. The results of comparison are tabulated below.

TABLE 1

| Properties | MG7-G1 | Streptomyces aburaviensis ISP 5033 |
|---|---|---|
| Form of aerial hyphae | Rectiflexibilis | Rectiflexibilis |
| Spore surface | Smooth | Smooth |
| Color of aerial hyphae | Grayish white to bright gray to brownish gray | Grayish white to gray to brownish gray |
| Color of growth | Pale yellow to pale yellowish brown to yellowish brown | Pale yellow to pale yellowish brown to dark yellow |
| Diffusible pigment | Negative or brown | Negative or brown |

TABLE 1-continued

| Properties | MG7-G1 | Streptomyces aburaviensis ISP 5033 |
|---|---|---|
|  | tinge | tinge |
| Chromogenicity: |  |  |
| on ISP-medium 1 | + | − |
| on ISP-medium 6 | No growth | − |
| on ISP-medium 7 | (+) | − |
| Hydrolysis of starch | + | + |
| Coagulation of milk | + | + |
| Peptonization of milk | + | + |
| Liquefaction of gelatine: |  |  |
| on plain gelatine | + | + |
| on glucose-peptone-gelatine | + | ± |
| Reduction of nitrate | ∓ | − |
| Utilization of carbon sources: |  |  |
| Glucose | + | + |
| L-arabinose | ∓ | − |
| D-xylose | − | −* |
| D-fructose | − | −* |
| Sucrose | − | − |
| Inositol | − | − |
| L-rhamnose | − | − |
| D-mannitol | − | − |

Note:
(+) means probably +; ± means slightly +; ∓ means probably −.
*means + in description of International Journal of Systematic Bacteriology.

As will be seen from the above table, the MG7-G1 strain is different from *Streptomyces aburaviensis* ISP 5033 in that (1) the former shows a positive chromogenicity whereas the latter show a negative chromogenicity on the ISP-media 1 and 7, that (2) the former does not grow on the ISP-medium 6 but grows thereon with formation of melanoid pigment when the iron ammonium citrate component has been removed from the ISP-medium 6, whereas the latter grows on the ISP-medium 6 without formation of melanoid pigment.

Although the MG7-G1 strain shows the properties different from those of *Streptomyces aburaviensis* in the above-mentioned points, they show the same properties in the other points, revealing that they are of the very closely related species. Streptomyces MG7-G1 strain was deposited in the Japanese public depository "Fermentation Research Institute", Agency of Industrial Science and Technology, Tukuba-gun, Ibaragi Prefecture, Japan under the deposit number FERM-P 5363 on and since Jan. 18, 1980 and also deposited in the American Type Culture Collection, Washington, D.C., U.S.A. under ATCC number 31860 and ATCC No. 31880.

Mutation of actinomycetes occurs frequently in either artificial or spontaneous conditions. Accordingly, this invention includes the use of the MG7-G1 strain as well as its variants and mutants as long as these produce ebelactone.

Ebelactone can be produced by aerobic cultivation of spores or mycelia of an ebelactone-producing strain of the genus Streptomyces, for example, Streptomyces MG7-G1 strain (identified as FERM-P 5363 or ATCC No. 31860 and ATCC No. 31880).

In carrying out the process of this invention, an amount of spores or mycelia of an ebelactone-producing strain is inoculated to a suitable culture medium therefor comprising assimilable carbon and nitrogen sources and is then incubated under aerobic conditions, preferably under submerged aerobic conditions, so that ebelactone is produced and accumulated in the culture broth. Generally, nutrient constituents of the culture media commonly employed for cultivation of ordinary actinomycetes can be used for the purpose of this invention. For instance, commercially available glycerin, glucose, lactose, sucrose, starch, maltose, molasses and other carbohydrates, fat and oil as well as a salt of a lower aliphatic acid such as malonic acid, maleic acid and the like are useful as the carbon source. Commercially available peptone, meat extract, cotton seed meal (e.g. Pharma-Media), peanut meal, soybean meal, yeast extract, N-Z amine, casein, L-asparagine, fish meal, sodium nitrate, ammonium nitrate, ammonium sulfate and the like may be useful as the nitrogen source. In addition, sodium chloride, phosphates, calcium carbonate, magnesium sulfate and other inorganic salts can be employed for the salt-additive in the culture medium. Other metal salts and various heavy metal salts may also be added in trace quantities, if required, as long as they are utilized by the ebelactone-producing strain and are not detrimental to the production of ebelactone. Any of the nutrient materials which are known for cultivation of actinomycetes may be employed in the process of this invention, as far as it is assimilable by the ebelactone-producing strain for the production of ebelactone.

Particularly, glycerin is preferred as the carbon source and fish meal and the like are preferred as the nitrogen source. A culture medium comprising 3.0% glycerin, 2.0% fish meal, 0.2% calcium carbonate is preferred for use.

For the production of ebelactone on a large scale, liquid cultivation is preferred. Any temperature at which the ebelactone-producing strain is able to grow and produce ebelactone can be employed for the cultivation, but a preferred incubation temperature is in a range of 20°~37° C., especially at 27° C. The cultivation is continued for a period of time sufficient to produce and accumulate a sufficient amount of ebelactone in the culture medium or broth. For instance, the production and accumulation of ebelactone reached a maximum at the end of incubation for 1 to 3 days when a culture medium comprising 3.0% glycerin, 2.0% fish meal, 0.2% calcium carbonate was prepared and sterilized, followed by inoculation with spores and mycelia harvested from a slant culture of the MG7-G1 strain and by shake-cultivation at 27° C. under aerobic conditions.

Tracing of ebelactone which is made during the course of cultivation of the ebelactone-producing microorganism as well as of recovery and purification of ebelactone may be achieved by determining the anti-esterase activity and the anti-formylmethionine aminopeptidase activity of ebelactone according to the following methods.

Firstly, assay of ebelactone for its anti-esterase activity can be made by determining the potency to inhibit esterase according to a modification of the method of C. Huggins and J. Lapides, "J. Biol. Chem." 170, 467 (1947). Thus, a commercially available esterase preparation obtained from pig liver (a product of Sigma Co., U.S.A.) is diluted with water to a 1000 folds volume, and the resulting esterase solution (0.025 ml) is admixed with 1 ml of 0.1 M phosphate buffered solution (pH 7.0) containing 0.06% "Triton X-100" (a trade name of an emulsifier consisting of a polyethyleneglycol alkylphenylether, a product of Rohm & Haas Co., U.S.A.) and 0.95 ml of water containing an ebelactone sample to be assayed, and the resulting mixed solution (1.975 ml) is admixed with 0.025 ml of a solution of 40 mM p-nitrophenyl acetate (the substrate) in methanol to start the reaction of p-nitrophenyl acetate with the esterase. After the enzymatic reaction is effected at room temperature for 20 minutes, absorbance (a) at 400 nm of the resulting reaction solution is measured. On the other hand, absorbance (b) at 400 nm of a control reaction solution containing no ebelactone is measured in the same way as above. Percent of inhibition to esterase is calculated according to the following equation:

Inhibition $(\%) = (b-a)/b \times 100$

In accordance with this assay method, the colorless crystalline product of ebelactone A (the product of Example 8 given hereinafter) had a potency such that its $ID_{50}$, namely the dose of giving 50% inhibition to esterase amounted to 0.056 mcg/ml, and the colorless crystalline product of ebelactone B (the product of Example 9 given hereinafter) had a potency such that its $ID_{50}$ amounted to 0.00035 mcg/ml.

Further, assay of ebelactone for its anti-formylmethionineaminopeptidase can be made according to the following method. Thus, as the substrate solution is employed a solution of N-formylmethionine β-naphthylamide (as the substrate) in methanol containing 5% (w/v) of "Tween" 20 (a trade name of a non-ionic surface-active agent, a product of Atlas Powder Co., U.S.A.). Formylmethionineaminopeptidase employed is that prepared from rat liver. The substrate solution (0.005 ml), 0.5 ml of 0.1 M Tris-hydrochloric acid buffered solution (pH 7.8) and 0.495 ml of water containing an ebelactone sample to be assayed are mixed together to a total volume of 0.95 ml. The reaction solution so obtained is further admixed with 0.05 ml of the enzyme solution, followed by effecting the enzymatic reaction at 37° C. for 25 minutes. After this, the reaction solution is admixed with 1 ml of a solution containing "Fast Garnet GBC" (a product of Sigma Co., U.S.A.) at a concentration of 1 mg/ml in a 1 M acetate buffered solution (pH 4.2) containing 10% of "Tween" 20, to stop the enzymatic reaction. After allowing to stand at ambient temperature for 15 minutes, absorbance (a) at 525 nm of the reaction solution is measured. On the other hand, adsorbance (b) at 525 nm of a control reaction solution obtained from the blank test is measured. Percent of inhibition to the formylmethionine aminopeptidase is calculated in a similar way to the above-mentioned method for determination of the potency for inhibition to esterase. In accordance with this assay method, the colorless crystalline product of ebelactone A had a potency such that its $ID_{50}$, namely the dose of giving 50% inhibition to the formylmethionine aminopeptidase amounted to 0.08 mcg/ml, and the colorless crystalline product of ebelactone B had a potency such that its $ID_{50}$ to said peptidase amounted to 0.02 mcg/ml.

Ebelactone may be produced well by a tank-cultivation method as well as by a shake-cultivation method. For instance, 1000 l of a liquid culture medium comprising 3.0% glycerin, 2.0% fish meal and 0.2% calcium carbonate was placed in a fermentation tank of 2000 l capacity and then sterilized, and the medium was inoculated with a slant culture of the MG7-G1 strain to an inoculum size of 2% while sterile air was passed at a rate of 800 l/minute through the culture medium which was agitated by stirrer rotating at 240 r.p.m. The incubation temperature was 27° C. In this experiment, production of ebelactone reached a maximum at the end of 37 hours of incubation. Ebelactone produced is present in the fermentation broth and also in the mycelia of the MG7-G1 strain. For recovery of ebelactone from the culture of the ebelactone-producing organism, the fermentation broth after completion of the incubation may be extracted with an equal volume of a water-immiscible organic solvent such as butyl acetate, butanol and the like by admixing the fermentation broth with the organic solvent and agitating the mixture for several hours to transfer ebelactone from the liquid phase of the culture and from the mycelia into the organic solvent phase. Ebelactone present in the fermentation broth filtrate may also be extracted into a water-immiscible organic solvent such as butanol, butyl acetate and the like, and ebelactone present in the mycelia may be extracted into a water-miscible organic solvent such as a methanol, ethanol and the like. It is also possible to recover ebelactone in a favorable yield from a solution containing this substance by adsorbing on a suitable adsorbent and desorbing therefrom. For this purpose, there may be employed an inorganic adsorbent, for example, activated carbon, alumina, silica gel and magnesium silicate (Frorigil), as well as organic adsorbent such as Amberlite XAD (a non-ionic, highly microporous resin, a product of Rohm & Haas Co., U.S.A.). For example, ebelactone may be adsorbed by silica gel and eluted therefrom using a mixed solvent of n-hexane-chloroform as eluant.

For isolation of ebelactone A from ebelactone B, it is especially effective to subject a mixture of ebelactones A and B to a column chromatography with a reverse phase chromatographing silica gel which is prepared by binding a silane with the surfaces of silica gel, where the elution is made using a mixed solvent of methanol-water as eluent. For instance, recovery and isolation of ebelactones A and B may be achieved in such a manner that the fermentation broth filtrate is extracted with a water-immiscible organic solvent such as butyl acetate, the butyl acetate extract is concentrated under reduced pressure to give an oily concentrate, this oil is purified by chromatography on silica gel and then further subjected to a column chromatography on silica gel developed with a suitable organic solvent system such as n-hexane-chloroform so as to afford the active fractions of eluate containing ebelactone A alone and the active fractions containing ebelactone B alone, and ebelactones A and B are separately isolated from the respective active fractions.

Final purification of ebelactone may be achieved by crystallization. As ebelactones A and B are each well crystallizable, they can be deposited as needles from a solution in a solvent system of methanol-water.

We have further researched on pharmacological properties of ebelactone, and as a result we have now found that ebelactone exhibits an activity to stimulate the immune response in a living animal by enhancing the cell-mediated immunity, as well as an activity to reduce inflammation in a living animal. The pharmacological properties of ebelactone are described below.

(1) Effect of ebelactone to enhance cell-mediated immunity.

Effect of ebelactone on the cell-mediated immunity was tested according to a known Delayed Type Hypersensitivity (D.T.H.) technique (see P. H. Lagrange, G. B. Mackaness and T. E. Mille: "J. Exp. Med.", 159, 1529–1539 (1974)) using mice immunized with sheep red blood cells (SRBC) as the antigen.

Thus, $10^8$ SRBC suspended in 0.05 ml of physiological saline solution were inoculated by subcutaneous injection to the one side of $CDF_1$ mice hind footpad (5 mice per group, female, 8-weeks old) to make immunization. At the same time as this immunization, 50 mg/kg, 12.5 mg/kg, 3.125 mg/kg or 0.781 mg/kg of ebelactone was intraperitoneally injected to each test mice. 4 Days later, $10^8$ SRBC were injected subcutaneously into the other side of each test mice hind footpad for elicitation of D.T.H. response. 24 Hours after the eliciting injection, the thickness (in mm) of the hind footpad was measured to evaluate the degree of the swelling in the footpad which received the eliciting injection of SRBC. The extent of the swelling in the footpad serves as a measure to estimate the cell-mediated immunity involved. The test results obtained are shown in Table 2 below.

TABLE 2

Effect of ebelactone on establishment of DTH. response to SRBC in mice

| Test Compound | Injection of antigen for immunization (0 day) | Dose of ebelactone (mg/kg) | Eliciting injection (4th day from immunization) | Foodpad thickness ($\times$ 0.1 mm) |
|---|---|---|---|---|
| Ebelactone B | $10^8$ SRBC | Intraperitoneal 0 (control) | $10^8$ SRBC | 7.4 |
| " | " | 50 | " | 12.2 |
| " | " | 12.5 | " | 13.3 |
| " | " | 3.125 | " | 13.6 |
| " | " | 0.781 | " | 14.2 |
| Ebelactone B | $10^8$ SRBC | Oral 0 (control) | $10^8$ SRBC | 8.1 |
| " | " | 0.5 | " | 14.1 |
| Ebelactone A | $10^8$ SRBC | 0.5 | $10^8$ SRBC | 12.2 |

From the results of the above table, it is found that administration of ebelactone in a dosage of 0.781-50 mg/kg by intraperitoneal injection or in a dosage of 0.5 mg/kg per os to mice remarkably enhances the development of DTH. Response and ebelactone shows a potentiating effect on cell-mediated immunity.

(2) Effect of ebelactone to reduce inflammation

Tests were made to estimate the suppressive effect of ebelactone and esterastin (U.S. Pat. Nos. 4,189,438 and 4,242,453) on the swelling of rat footpad caused by injection of carragheenin when the test compounds were administered orally and intraperitoneally to the test animal, Wister rats (male, body weight:140 to 150 g). The test compound was dissolved in about 0.5 ml of ethanol with addition of one drop of a non-ionic surface-active agent "Tween" 80, and the test compound solution in ethanol was diluted with an aqueous gum arabi to prepare an aqueous suspension containing the test dose of ebelactone or esterastin. The test sample suspension so prepared was then administered orally or intraperitoneally to the rats. One hour later, 1% aqueous carragheenin was injected subcutaneously to the footpad to bring about inflammation. After the injection of carragheenin, the volume of the footpad was measured twice, namely at the end of 3 hours and at the end of 5 hours from the carragheenin injection. For control test, the ebelactone or esterastin was omitted in the above test. Degree (%) of suppression of swelling was calculated from the measured volumes of the inflammated footpad. The results obtained are tabulated in Tables 3 and 4 below.

TABLE 3

Suppressive effect on inflammation of ebelactone and esterastin orally given

| Test Compound | Degree (%) of suppression of swelling | |
|---|---|---|
| | 3 Hours | 5 Hours |
| Gum arabic (Control) | — | — |
| Esterastin (50 mg/kg) (Comparative) | 10.3% | −3.0% |
| Ebelactone B (10 mg/kg) | 11.2% | 8.2% |
| Ebelactone B (50 mg/kg) | 11.6% | 7.8% |
| Ebelactone B (100 mg/kg) | 7.0% | 9.6% |

TABLE 4

Suppressive effect on inflammation of ebelactone and esterastin intraperitoneally administered

| Test Compound | Degree (%) of suppression of inflammation | |
|---|---|---|
| | 3 Hours | 5 Hours |
| Gum arabic (Control) | — | — |
| Esterastin (30 mg/kg) (Comparative) | 31.1% | 28.1% |
| Ebelactone B (5 mg/kg) | 17.1% | 8.8% |
| Ebelactone B (10 mg/kg) | 9.1% | 10.0% |
| Ebelactone B (30 mg/kg) | 50.6% | 20.9% |
| Ebelactone A (30 mg/kg) | 45.9% | 18.5% |

From the above tables, it is noted that upon oral administration of ebelactone B, a significant reduction in the degree of swelling as compared to that of the control test group could be achieved both at the ends of 3 hours and 5 hours from the carragheenin injection with dosage of 10 mg/kg of ebelactone B; at the end of 3 hours from the carragheenin injection with dosage of 50 mg/kg of ebelactone B; and at the end of 5 hours from the carragheenin injection with dosage of 100 mg/kg of ebelactone B. Furthermore, it is noted that upon intraperitoneal administration of ebelactone, a significant reduction in the degree of swelling as compared to that of the control test group could be obtained with all dosages of ebelactones A and B and at all the times of evaluation, except at the end of 5 hours with dosage of 5 hours with dosage of 5 mg/kg and at the end of 3 hours with dosage of 10 mg/kg of ebelactone B. Similar results could be observed also in the anti-inflammation tests with ebelactone A.

From further tests, it is also revealed that ebelactone at a concentration of 100 mcg/ml exhibits no cell-toxicity to the tissue-cultured cells, and that dosage of 250 mg/kg of ebelactone (intraperitoneally) does not give any sympton of toxicity at all in the test of estimating acute toxicity in mice.

These and above-mentioned results show that ebelactone is of a low toxicity and is useful as a pharmaceutical agent which may be utilized with high safety, and that ebelactone is useful at least as an agent of potentiating the cell-mediated immunity.

According to a third aspect of this invention, therefore, there is provided a pharmaceutical composition comprising a safe and effective amount of at least one of ebelactones A and B, in admixture with a pharmaceutically acceptable carrier.

According to a further aspect of this invention, there is provided a host defense stimulator for enhancing mainly the immune response in a living animal, which comprises as the active ingredient at least one of ebelactones A and B, in combination with a pharmaceutically acceptable carrier for the active ingredient.

This invention further provides a method for stimulating the immune response in a living animal, which comprises administering a safe and immunopotentiatingly effective amount of at least one of ebelactones A and B to said animal.

According to another aspect of this invention, there is provided an anti-inflammatory composition for treating inflammation in a living animal, which comprises as the active ingredient at least one of ebelactones A and B, in combination with a pharmaceutically acceptable carrier for the active ingredient. There is further provided a method for treating inflammation in a living animal, which comprises administering a safe and anti-inflammatorily effective amount of at least one of ebelactones A and B to said animal.

The pharmaceutical composition of this invention, either as the host defense stimulator or as the anti-inflammatory agent, may be formulated as conventional orally administrable forms such as tablets, capsules, powders, solutions and suspensions, either by admixing an amount of ebelactone with a conventional pharmaceutically acceptable solid carrier such as starch, sucrose, talc and calcium carbonate or by dissolving or suspending an amount of ebelactone in a pharmaceutically acceptable liquid carrier such as ethanol and water. The proportion of ebelactone to the solid or liquid carrier may be chosen appropriately depending on the form of the orally administrable formulation prepared and usually may be in a ratio of from 1:1 to 1:100 by weight.

The composition of this invention may also be formulated into injectable solutions or suspensions by dissolving or suspending ebelactone at a suitable level of from 0.1% to 10% by weight into a physiological saline solution or other conventional pharmaceutically acceptable liquid vehicle such as Ringer's solution, with or without aid of a suitable dispersion agent. The injectable solution or suspension so prepared may be given, eg. by intravenous injection, intramuscular injection or intraperitoneal injection.

It will be appreciated that the actual preferred dosage of ebelactone used will vary according to the particular composition formulated for administration, the mode of administration and the particular disease to be treated. Many factors that modify the action of the drug of this invention will be taken into account by the skilled in the art, for example, age, body weight, sex, diet, time of administration, route of administration, rate of excretion, drug combinations, reaction sensitivities and severity of the disease. Generally, about 0.5 mg/kg to about 100 mg/kg of ebelactone may be given a day to adult person. Optimal dosages for a given set of conditions of a patient can be ascertained by the skilled in the art using conventional dosage determination tests in view of the above guidelines and in view of the past experiences as obtained when determining suitable dosages of the previously known drugs.

It is believed that using the preceding description and without further elaboration, one skilled in the art can utilize the concept of this invention to its full extent. The following preferred specific embodiments are, therefore, to be construed as merely illustrative of this invention.

EXAMPLE 1

A loopful amount of a slant culture of Streptomyces MG7-G1 strain (identified as FERM-P 5363 or ATCC. No. 31860 and ATCC No. 31880) as the ebelactone-producing strain was inoculated to 15 liters of a culture medium comprising 3.0% glycerin, 2.0% fish meal and 0.2% calcium carbonate which had been placed in 110 ml portions in rotary flasks of 500 ml capacity and which had been sterilized by heating at 120° C. for 20 minutes. The incubation was conducted for consecutive 10 days at 27° C. and at a rotation speed of 180 r.p.m., while samples were taken out of the incubated medium at an interval of times and each sample was assayed for the potency of ebelactone to observe how the production of ebelactone proceeded during the incubation period. On the 2nd day of incubation, the production of ebelactone reached a maximum, and the level of the esterase-inhibiting substance in the incubation medium decreased slowly since the 3rd day of incubation. The pH value of the incubated medium varied from 7.0 on the 1st day, to 6.6 on the 2nd day, to 7.3 on the 3rd day, to 7.8 on the 4th day and to 8.2 on the 5th day of incubation.

EXAMPLE 2

Streptomyces MG7-G1 strain (FERM-P 5363 or ATCC No. 31860 and ATCC No. 31880) was cultivated for 2 days using the same culture medium and incubation conditions as those in Example 1, and the fermentation broth (2.5 l, the antiesterase activity, $ID_{50}$: 1 µg/ml) so obtained was admixed with 2.5 l. of butyl acetate. The resultant mixture was agitated at ambient temperature for 2 hours, followed by filtration with aid of a filtration-aid (diatomaceous earth, commercially available under a tradename "Hyflo-Supercel"). The filtrate obtained was separated into the butyl acetate phase and the aqueous phase. The butyl acetate phase was concentrated under reduced pressure to give 4.36 g of an oily product comprising ebelactone.

EXAMPLE 3

The oily product (4.36 g) obtained in Example 2 and containing ebelactone was chromatographed in a column (2.5×35 cm) of a silica gel (Wako Gel C-200, a product of Wako Chemical Co., Japan) using a mixed solvent of n-hexane-chloroform-ethyl acetate (5:5:1 by volume) as eluent. The eluate was collected in 10 g-fractions, and the fraction Nos. 41-137 were found to contain the active substance, ebelactone. These active fractions as combined together were concentrated to dryness under reduced pressure to yield a lightly yellow colored oily product. Yield 434 mg.

EXAMPLE 4

The oily product (434 mg) obtained in Example 3 was chromatographed in a column (1.2×47 cm) of the reversed-phase silica gel (Silicagel 60, Silanized, a product of Merck Co., West Germany) using a mixed solvent of methanol-water (1:1 by volume) as eluent. The eluate was collected in 10 ml-fractions, and there were obtained the active fraction Nos. 38–53 containing ebelactone A, and the active fraction Nos. 65–81 containing ebelactone B. These active fractions were combined together, respectively and concentrated under reduced pressure to give 20 mg of a colorless powder of ebelactone A and 10 mg of a colorless powder of ebelactone B, respectively. These ebelactone products gave a single spot (Rf 0.72 and 0.80, respectively) when developed in a silica gel thin layer chromatography with a mixed solvent of n-hexane-chloroform-ethyl acetate (5:5:1 by volume).

EXAMPLE 5

A culture medium (1000 l) comprising 3.0% glycerin, 2.0% fish meal, 0.2% calcium carbonate and 0.01% antifoaming agent (polyoxyalkylene commercially available under a tradename "Adecanol", a product of Asahi Denka Co., Japan) was charged in a stainless steel tank of 2000 l capacity and then sterilized by heating at 120° C. for 30 minutes. To this sterilized culture medium was inoculated 50 l of a seed culture which was obtained by incubating Streptomyces MG7-G1 strain (FERM-P 5363) for 2 days at 28° C. under aeration and agitation. The inoculated culture medium was incubated at 28° C. for 43 hours at a rate of aeration of 80 l/minutes and at an agitator speed of 240 r.p.m. The fermentation broth so obtained was admixed with 350 l of butyl acetate and then agitated for 4 hours, followed by decantation and filtration with aid of a filtration-aid (Hyflo-Supercel) and by means of a basket-centrifugator to remove the mycelia. The butyl acetate phase was removed in this way and then concentrated under reduced pressure to afford 1.9 liters of a concentrated solution containing ebelactone.

EXAMPLE 6

The concentrated solution (1.9 l) obtained in Example 5 and containing ebelactone was placed in a column (10×60 cm) of silica gel (Wako Gel C-100, a product of Wako Chemical Co., Japan), which was then washed by passing 7 l of n-hexane therethrough. The column was subsequently developed with 4.5 l of n-hexane-chloroform (1:1 by volume) and then with 10 l of n-hexane-chloroform-ethyl acetate (5:5:1 by volume) as eluent. The eluate was collected in 50 ml-fractions, and the active fractions Nos. 81–200 were obtained. These active fractions were combined together and concentrated to give 150.9 g of an oily product.

EXAMPLE 7

The oily concentrate (71.6 g) obtained in Example 6 and containing ebelactone was chromatographed in a column (5.5×17.5 cm) of a reversed-phase silica gel (Silicagel 60, Silanized, a product of Merck Co., West Germany) using a mixed solvent of methanol-water (1:1 by volume) as eluent. The eluate was collected in 20 ml-fractions.

When examined by a thin layer chromatography, ebelactone A was detected mainly in the fraction Nos. 105–147 in which ebelactone B could not be detected. Ebelactones A and B were both detected in the fraction Nos. 148–270. Ebelactone B was detected mainly in the fraction Nos. 271–443 in which ebelactone A could not be detected. The combined fraction Nos. 105 to 147, the combined fraction Nos. 148 to 270 and the combined fraction Nos. 271 to 443 were concentrated under reduced pressure to give 392 mg of a yellow powder, 974 mg of a yellow powder and 518 mg of a yellow powder, respectively.

EXAMPLE 8

The yellow powder (392 mg) obtained in Example 7 and mainly containing ebelactone A was chromatographed in a silica gel column (Wako Gel C-300, a product of Wako Chemical Co., Japan, 1.3×48 cm) using a mixed solvent of n-hexane-chloroform (3:1 by volume) as eluant. The eluate was collected in 5 g-fractions, and the active fraction Nos. 101–130 were combined together and concentrated under reduced pressure to afford 175 mg of a colorless powder of ebelactone A which gave a single spot (Rf 0.72) in a silica gel thin layer chromatography with a mixed solvent of n-hexane-chloroform-ethyl acetate (5:5:1 by volume). This colorless powder was dissolved in a small volume of methanol, and to the resulting methanolic solution was added in small portions a volume of water to yield 128 mg of a needles of ebelactone A. m.p. 86° C. This crystalline product of ebelactone A had a potency of 0.056 mcg/ml for its $ID_{50}$ to esterase.

EXAMPLE 9

The yellow powder (518 mg) obtained in Example 7 and mainly comprising ebelactone B was chromatographed in a silica gel column (Wako Gel C-300, a product of Wako Chemical Co., Japan, 1.3×50 cm) using a mixed solvent of n-hexane-chloroform (3:1 by volume) as eluant. The eluant was collected in 10 g-fractions, and the active fractions Nos. 49–58 were combined together and concentrated under reduced pressure to afford 219 mg of a colorless powder of ebelactone B which gave a single spot (Rf 0.80) in a silica gel thin layer chromatography with a mixed solvent of n-hexane-chloroform-ethyl acetate (5:5:1 by volume). This colorless powder was taken up into a small volume of methanol, and to the resulting solution in methanol was added in small portions a volume of water to yield 129 mg of needles of ebelactone B. m.p. 77° C. This crystalline product of ebelactone B had a potency of 0.00035 mcg/ml for its $ID_{50}$ to esterase.

What we claim is:

1. The new compound, ebelactone which is selected from ebelactone A and ebelactone B according to the general formula

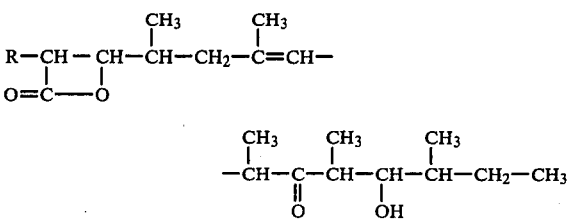

wherein R is methyl group —CH₃ for ebelactone A and ethyl group —CH₂CH₃ for ebelactone B.

2. Ebelactone A of the formula

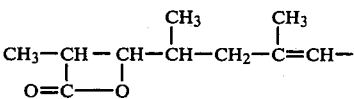

-continued

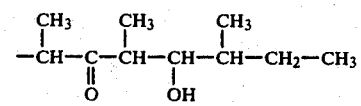

3. Ebelactone B of the formula

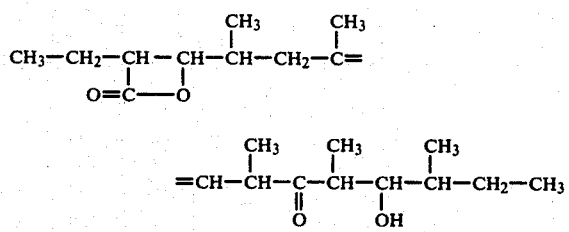

4. The process for the production of ebelactone, which comprises cultivating an ebelactone-producing strain of the genus Streptomyces under aerobic conditions in a culture medium containing assimilable carbon and nitrogen sources for a sufficient time to produce and accumulate ebelactone in the culture medium.

5. The process as claimed in claim 4 which comprises further a step of recovering ebelactone from the culture medium.

6. The process as claimed in claims 4 or 5 in which the ebelactone-producing strain is Streptomyces MG7-G1 identified as FERM-P 5363.

7. The process for the production of ebelactone A which comprises cultivating an ebelactone A-producing strain of Streptomyces under aerobic condtions in a culture medium containing assimilable carbon and nitrogen sources for a sufficient time to produce and accumulate ebelactone A in the culture medium.

8. The process for the production of ebelactone B which comprises cultivating an ebelactone B-producing strain of Streptomyces under aerobic conditions in a culture medium containing assimilable carbon and nitrogen sources for a sufficient time to produce and accumulate ebelactone B in the culture medium.

9. The process as claimed in claim 7 or 8 in which Streptomyces MG7-G1 is cultivated at a temperature of 20° to 37° C. for 1 to 3 days.

* * * * *